United States Patent [19]

Grane et al.

[11] 4,294,999

[45] Oct. 13, 1981

[54] PREPARING OXYGEN-CONTAINING FUEL WHEREIN TERTIARY BUTYL ALCOHOL IS THE MAJOR PRODUCT OF THE PROCESS

[75] Inventors: Henry R. Grane, Springfield; John C. Jubin, Jr., Wallingford; G. Richard Worrell, Media, all of Pa.

[73] Assignee: Atlantic Richfield Company, Los Angeles, Calif.

[21] Appl. No.: 124,035

[22] Filed: Feb. 25, 1980

Related U.S. Application Data

[63] Continuation-in-part of Ser. No. 45,454, Jun. 4, 1979, abandoned.

[51] Int. Cl.³ .............................................. C07C 29/50
[52] U.S. Cl. ........................................ 568/910; 44/54
[58] Field of Search ........................................ 568/910

[56] References Cited

U.S. PATENT DOCUMENTS

| | | | |
|---|---|---|---|
| 2,653,962 | 9/1953 | Mitchell et al. | 568/910 |
| 2,845,461 | 7/1958 | Winkler et al. | 568/910 |
| 2,862,973 | 12/1958 | Winkler et al. | 568/910 |
| 3,360,585 | 12/1967 | Winnick | 568/910 |
| 3,391,214 | 7/1968 | Fetterly | 568/910 |
| 3,470,239 | 9/1969 | Russell | 568/910 |
| 3,478,108 | 11/1969 | Grane | 568/910 |
| 3,816,548 | 6/1974 | Williams et al. | 568/910 |
| 3,825,605 | 7/1974 | Johnston | 568/910 |
| 3,829,510 | 8/1974 | Adams et al. | 568/910 |
| 3,836,603 | 9/1974 | Conner et al. | 568/910 |

FOREIGN PATENT DOCUMENTS 1016035  1/1966  United Kingdom ................ 568/910

OTHER PUBLICATIONS

Winkler et al., "Ind. & Eng. Chem." vol. 53 (1961), pp. 655-658.

*Primary Examiner*—Joseph E. Evans
*Attorney, Agent, or Firm*—John R. Ewbank

[57] ABSTRACT

Isobutane is oxidized in a pressurized reactor in the presence of a solubilized molybdenum catalyst to produce a mixture of tertiary butyl alcohol, tertiary butyl hydroperoxide, methanol, acetone, and other oxygen containing compounds. Unreacted isobutane is recycled. Streams of normally gaseous components, comprising carbon dioxide and carbon monoxide are withdrawn from the effluent streams. A liquid stream withdrawn from the reactor, after being debutanized, is subjected to a thermal decomposition zone under several atmospheres pressure at about 280° F. for from 2 to about 8 hours to reduce the concentration of tertiary butyl hydroperoxide.

The liquid derived from the decomposition zone is distilled to provide a distillate stream comprising predominantly tertiary butyl alcohol and a minor proportion of methanol. Said distillate stream is heat treated to destroy residual TBHP and then transferred to a gasoline blending zone in which it is added to hydrocarbons. Said oxygen-containing fuel is blended as if it were a technical grade of tertiary butyl alcohol, notwithstanding the fact that measurable amounts of acetone, methanol, and/or related oxygen containing compounds might be present.

2 Claims, 1 Drawing Figure

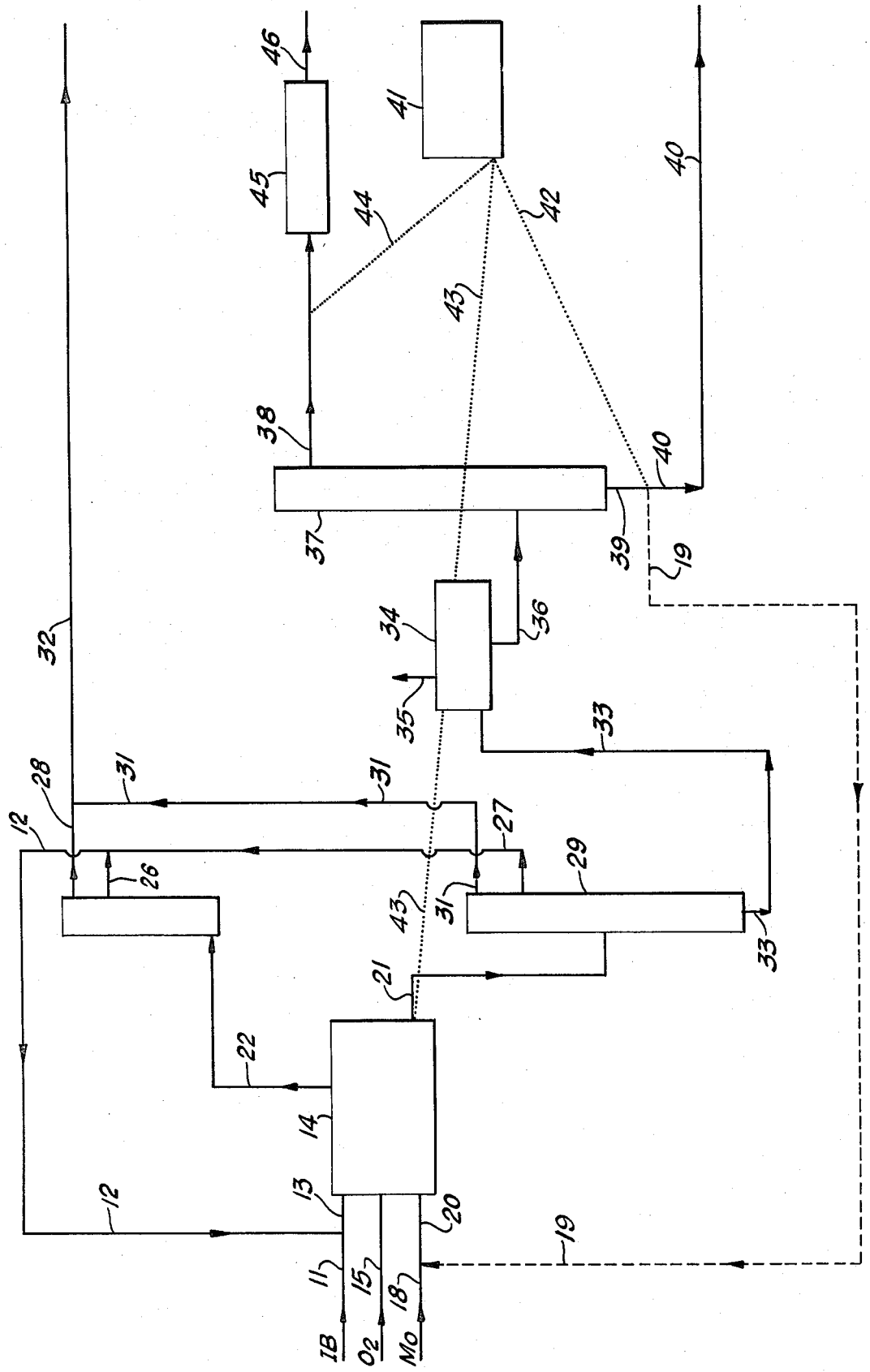

PREPARING OXYGEN-CONTAINING FUEL WHEREIN TERTIARY BUTYL ALCOHOL IS THE MAJOR PRODUCT OF THE PROCESS

RELATED APPLICATIONS

This is a continuation-in-part of Ser. No. 45,454 filed June 4, 1979, and now abandoned.

Reference is made to the related applications of Henry R. Grane, John C. Jubin and G. Richard Worrell, all the disclosure of which is deemed here reiterated and incorporated herein, said application including "MANUFACTURE OF TERTIARY BUTYL ALCOHOL", Ser. No. 045,365 filed June 4, 1979, now abandoned, and "REMOVING WATER FROM TERTIARY BUTYL ALCOHOL", Ser. No. 051,561, filed June 25, 1979, now U.S. Pat. No. 4,239,926.

FIELD OF INVENTION

This invention relates to the preparation of mixtures containing a predominant amount of tertiary butyl alcohol (TBA) by the oxidation of isobutane, and to the utilization of a mixture comprising tertiary butyl alcohol as a component in a blended gasoline.

BACKGROUND OF THE INVENTION

Loder, U.S. Pat. No. 2,265,948 employs acetic acid as the solvent for oxidizing isobutane to TBA.

Robertson et al, U.S. Pat. No. 2,780,654 employs benzene as a solvent in oxidizing a mixture of isobutane and isobutene to a mixture of TBA and isobutylene glycol.

Winkler et al, U.S. Pat. No. 2,845,461 oxidizes liquid isobutane in the absence of catalyst to prepare a mixture of TBA and tertiary butyl hydroperoxide (TBHP).

Grane, U.S. Pat. No. 3,474,151 heats TBA at 375°–475° F. for a few minutes, whereby traces of TBHP are thermally decomposed to provide a TBA suitable for blending into gasoline.

Johnston, U.S. Pat. No. 3,825,605 oxidizes isobutane to TBA using a solid catalyst comprising molybdenum oxide, and minor amounts of two other metals (from a group comprising cobalt, iron, or chromium).

Kozlowski et al, U.S. Pat. No. 3,832,149 prepares a motor fuel consisting of a mixture of alkylate and an oxylate prepared by hydrogenating the oxidate derived from oxidizing isobutane.

Barone, U.S. Pat. No. 3,974,228, employs a buffer such as lanthanum carbonate in oxidizing isobutane to TBHP.

Brownstein et al, U.S. Pat. No. 4,028,423 oxidizes isobutane to TBA and TBHP using a copper polyphthalocyanine catalyst activated with an aromatic amine.

There is a demand for an advantageous method of preparing an oxygen-containing fuel component consisting largely of tertiary butyl alcohol by the oxidation of isobutane.

SUMMARY OF INVENTION

In accordance with the present invention, isobutane is oxidized to produce a liquid effluent comprising both tertiary butyl alcohol (TBA) and tertiary butyl hydroperoxide (TBHP) in the presence of from 1 to 1000 parts of soluble molybdenum catalyst per million parts of isobutane. The temperature must be maintained within the range from 240° F. to 310° F. at a pressure within the range from 200 to 1000 psig at a residence time within a range from about 3 to 10 hours. The effluent from such oxidation zone is debutanized and subjected to decomposition of a portion of the TBHP. The effluent from the decomposition zone is distilled to recover a fraction from the overhead stream comprising TBA, methanol, and acetone, and to provide a residual liquid containing soluble molybdenum catalyst, the unit weight ratio of TBA to TBHP in said residual liquid being greater than one, the amount of TBA in the residual liquid being a small fraction of the amount of TBA in said distillate fraction.

The invention is further clarified by reference to a plurality of embodiments.

DESCRIPTION OF EMBODIMENTS

EXAMPLE I

The oxidation zone is in a pressurized reactor which is partially filled with a liquid reaction mixture comprising 5 ppm of soluble molybdenum catalyst. The liquid reaction mixture can be deemed to be about 66% isobutane and about 34% of a liquid mixture of oxidate, comprising products and byproducts. Fresh isobutane is injected and recycle isobutane is injected into the liquid reaction mixture. An oxygen-containing gas is injected into the liquid reaction mixture. The reactor is maintained at 700 psig and at 280° F. The average residence time for the isobutane in the reactor is about 4 hours, and the extent of conversion of the isobutane is about 34%. The yields of byproducts and products from such oxidation of isobutane correspond to about 66% tertiary butyl alcohol (TBA), about 22% tertiary butyl hydroperoxide (TBHP), about 6% acetone, about 6% of a mixture comprising about 2% water, about 1.5% methanol and minor amounts of related components. About 1% of the isobutane is converted to carbon dioxide with a measurable amount of carbon monoxide.

The reactor is maintained and operated in the manner corresponding generally to the operation of a reactor for production of a mixture featuring TBHP (but also comprising TBA) except that a molybdenum catalyst is present and the product is withdrawn at a more rapid rate so that the residence time is only 4 hours and thus less than standard industrial practice when TBHP is the product which is particularly desired. The liquid reaction mixture is adequately agitated so that the average composition of the reaction mixture and the composition of the liquid effluent from the reactor are treated as identical.

The liquid stream withdrawn from the oxidation zone is directed through a plurality of stages of debutanization so that isobutane is separated from the reactor effluent and directed toward the pumps which recycle the isobutane to the reactor.

The debutanized mixture from the oxidation zone is directed to a decomposition zone in which the TBHP undergoes a decomposition to form predominantly TBA and oxygen. The decomposition zone residence time is four hours and oftentimes approximately the same as in the oxidation zone. The temperature is about 260° F., and the pressure is about 50 psig. Some of the decomposition of the TBHP leads to the formation of a mixture of methanol and acetone. From the decomposition of 20 of the 22 parts pf TBHP, the product stream comprises about 13.5 parts of TBA, about 1 part of water, about 2 parts of methanol, about 1.5 parts of acetone, about 2 parts of gas and about 2 parts of TBHP. The decomposition of the TBHP is not complete so that the residual liquid contains about 2 parts of TBHP. The combination of the oxidation reaction and the decomposition reaction leads to the formation of about 79.5 parts of TBA, 2 parts of TBHP, 8.5 parts of acetone, 3 parts of methanol, 2 parts of water, 2 parts of other liquid byproducts, and 3 parts of gas.

The liquid withdrawn from the decomposition reactor is directed to a distillation zone from which is removed an overhead stream conveniently called a distillate which may comprise acetone, methanol and TBA. Particular attention is directed to the fact that the weight ratio of TBA to TBHP in the residual liquid is generally slightly greater than 1:1. Such dilution of the TBHP in a greater weight concentration of TBA prevents the development of a hazardous concentration of TBHP. The amount of TBA in the residual liquid is a small fraction of the distilled TBA. Only small amounts of TBHP survive the decomposition zone.

The distillate from said distillation zone, said distillate consisting predominantly of TBA containing acetone and methanol, sometimes contains trace amounts of TBHP. The octane rating and motor fuel performance of TBA can be significantly impaired by the presence of relatively small amounts of TBHP. Accordingly, after such distillation of TBA, it is subjected to the "cleanup" procedure of Grane U.S. Pat. No. 3,474,151 for decreasing the TBHP concentration to an acceptably low level. Such cleanup treatment consists of heating the TBA and maintaining it within the 375°–475° F. (desirably 400°–450° F.) range for from 1 to 10 (desirably 5–9) minutes. For example, the TBA stream can be heated at 406° F. for 8 minutes at 600 psig, or at 419° F. for 3 minutes at 600 psig.

Said residual liquid contains polybdenum catalyst, but the value thereof is low enough that discarding such residual liquid is permissible from an engineering cost standpoint. If desired, a portion of such residual liquid can be recycled to the reactor, with the withdrawal of enough residual liquids to prevent the build up of excessive amounts of components (other than TBHP) boiling above TBA and/or not codistilling with the TBA. Such high boiling components should not exceed about 8% by weight of the liquid in the oxidation zone.

EXAMPLE II

It is possible to employ one form of laboratory reactor consisting of a large pressurized kettle (autoclave) in which a stirrer maintains a reasonably uniform liquid mixture while reactants are injected into such liquid reaction mixture and a liquid stream of the reaction mixture is withdrawn from a zone different from the various zones at which reactants are injected. A liquid level control can maintain the amount of liquid in the autoclave at a predetermined height so that the rate of removal of reaction mixture responds to the combination of factors comprising reaction rate and reactant injection rate. Air is injected into the liquid to oxidize components, thereby forming a nitrogen-containing effluent gas. A reflux condenser desirably is positioned so that all liquid components boiling above carbon dioxide are refluxed back into the reaction mixture. The exit vapor stream consists predominantly of a mixture of carbon dioxide, carbon monoxide, oxygen, and nitrogen, and it is this vapor stream which actuates the automatic pressure regulator, permitting an exit flow rate of such vapor stream sufficient to prevent development of excess pressure. All of the gas withdrawn from the gas pressure regulator is relatively free of hydrocarbons (most notably isobutane). A pressure of 800 psig was used in the described experimental work, but a wider pressure range can be operable. Previous work has shown that within a range from about 200 psig to 1000 psig the effect of pressure on the reaction rate is not significant. It is important that there be both a liquid phase and a vapor phase and a stable liquid level (freedom from troublesome frothing) in the reactor.

A series of tests are conducted while maintaining a uniform liquid residence time. In a control test in the absence of a molybdenum catalyst, the temperature is maintained at 270° F. with the pressure maintained at 800 psig, and a pure grade of isobutane is the feedstock. The conversion of isobutane is 23.2% and 76.8% of the isobutane feed is recovered in the liquid effluent from the reactor. The tertiary butyl alcohol is 38.9% of the liquid oxidate (mixture of TBHP and TBA) in such control, thus providing selectivity for TBHP of 61.1 weight percent.

In accordance with the present invention, a feedstock consisting of 100% isobutane is fed to the same stirred, pressurized kettle at 300° F. at 1000 psig. The feedstock is injected into the reaction mixture and liquid reactor contents are withdrawn at a rate for maintaining about half the residence time of the control test. This preparation of TBA, in accordance with the present invention, is regulated to be closely similar to said control except for the use of higher temperatures and pressures and the use of about 100 ppm of soluble molybdenum catalyst, and the use of a shorter residence time. In both cases, air is injected into the liquid contents of the reactor and unreacted oxygen and nitrogen as well as carbon dioxide byproduct are withdrawn through the outlet of the pressure control system. The results obtained from both tests are shown in Table 1.

TABLE 1

| Effect of Altering Catalyst, Temperature and Residence Time | | | |
|---|---|---|---|
| | Control | Ex. 2 | Dif. |
| Exp. Conditions | | | |
| Reactor Temp. °F. | 270 | 300 | +30 |
| Reactor Press. psig | 800 | 1000 | +200 |
| TBA Production | | | |
| Selec. as Wt. % of TBA formed per wt. of oxidate formed | 38.9 | 75.0 | +36.1 |

Liquid is withdrawn from the oxidation reactor and directed through multiple stages of pilot plant debutanization, with the isobutane being pumped back to the oxidation reactor. The debutanized effluent at about 100 psig is directed to the decomposition reactor, an autoclave functioning in a manner generally similar to the autoclave employed as the oxidation reactor. The debutanized effluent is maintained in the decomposition reactor for about 3.5 hours residence time. The withdrawn stream consists of a mixture of about 80% TBA, about 2% TBHP, about 7% acetone, about 2% methanol, about 2% water, about 3% other liquid byproducts, and about 4% gas. The liquid is distilled to provide a distillate stream comprising TBA, acetone, and methanol, and the residual liquid can be directed for use as a component of fuel oil in an industrial burner in which the high molybdenum concentration is tolerable. Said residue contains a minor amount of TBHP, a greater weight of TBA than TBHP, other liquid byproducts, and molybdenum catalyst.

Said distillate stream is subjected to a cleanup treatment by heating it to 406° F. for eight minutes to decompose the TBHP, thus providing a TBA rich fuel component, suitable for blending with naphtha and reformate to prepare gasoline, and to enhance the octane thereof.

EXAMPLES III-IV

The apparatus and system of Example II, comprising the pressure-regulated, liquid level regulated, temperature-regulated autoclaves for both the oxidation reaction and for the decomposition reaction, are employed, together with multi-stage debutanizer, distillation zone, cleanup heating zone, and gasoline blending zone, in an effort to determine operable limits for the manufacture of TBA.

By a series of experiments, it is established that the oxidation zone must be operated to produce a weight ratio of TBA to TBHP of at least 2 to 1, and that the concentration of the soluble molybdenum oxide catalyst must be within the range from about 1 to about 1,000 parts per million by weight (i.e., from 0.0001% to 0.1%).

The procedures for preparing TBA rich mixture useful for blending into gasoline, following the general procedure of Example II, but modifying some of the process variables, are followed as indicated in Table 2.

TABLE 2

|  | Examples | |
| --- | --- | --- |
| Oxidation Reactor Cond. | 3 | 4 |
| Pressure psig | 600 | 500 |
| Temperature °F. | 290 | 500 |
| Residence Time, hr. | 3 | 5 |
| Ppm Mo | 2 | 4 |
| Decomposition Reactor Conditions | | |
| Pressure psig | 60 | 90 |
| Temperature | 300 | 250 |
| Residence Time | 3 | 5 |
| Oxidation | | |
| Conversion % | 30 | 45 |
| Liquid Selec. % | 98 | 99 |
| Debutanized Effluent from Oxidation Reactor % by Weight | | |
| TBA | 61.1 | 63.4 |
| TBHP | 25.2 | 24.3 |
| Acetone | 7.0 | 6.3 |
| Methanol | 1.6 | 1.5 |
| Others | 2.3 | 2.1 |
| Water | 2.8 | 2.4 |
| Effluent from Decompsition Reactor | | |
| TBA | 80 | 78 |
| TBHP | 2 | 2 |
| Acetone | 8 | 9 |
| Methanol | 4 | 5 |
| Others | 3 | 3 |
| Water | 3 | 3 |

In the drawing, a stream of fresh isobutane 11 combines with a recycle IB stream 12 to provide a merged IB stream 13 directed into an oxidation zone 14. The temperature is maintained in the 240°-310° F. range at liquid phase conditions of 200-1000 psig at a 3-10 hour residence time at a 1-1000 ppm of molybdenum catalyst concentration. Fresh oxygen stream 15 is directed into the oxidation zone 14. Molybdenum catalyst stream 18 may, if desired, be merged with an optional catalyst recycle stream 19 (usually zero) before catalyst stream 20 enters reactor. Obviously various modifications of mixing and/or injection approaches are feasible, and the drawing is highly schematic to permit a general perspective on the overall process. For example, nitrogen can be included in the $O_2$ stream, as indicated by its presence in the exit gas stream.

In oxidation reaction zone 14, IB is oxidized to produce high boiling components (HBC) tertiary butyl hydroperoxide (TBHP), tertiary butyl alcohol (TBA), methanol (MeOH), acetone ($Me_2CO$), carbon dioxide ($CO_2$) and carbon monoxide (CO). The reaction mixture comprises all said reactants and all said products, and is sufficiently well agitated that the composition of a slip stream 21 from oxidation zone 14 can be deemed to have the same composition as the lower liquid layer in oxidation zone. Above the liquid and froth is a vapor zone. An overhead stream 22 permits withdrawal from oxidation zone of a mixture comprising nitrogen, oxygen, carbon monoxide and carbon dioxide. Such overhead stream may comprise isobutane scheduled for recycling, or the reflux controls may purify the overhead stream to eliminate recycling of isobutane from the overhead except as reflux. It is convenient to conduct a series of successive steps in a fractional distillation tower, but a series of dephlegmators could promote an equivalent series of selective condensation steps. Thus, the purification of overhead stream 22 involves selective condensation steps. If isobutane is selectively condensed from the overhead vapor stream, then the resulting overhead IB stream 26 is merged with an isobutane stream 27 derived from slip stream 21 to provide the IB recycle stream 12.

A gaseous withdrawal stream 28 comprises nitrogen (present in at least measurable amounts in the air, commercial oxygen, mixture, or other $O_2$ feed stream 15), carbon monoxide, and carbon dioxide. As has been true of the gaseous withdrawal stream from liquid isobutane oxidation zones for many years, the equilibrium ratio of oxygen to carbon dioxide present in the vapor space of oxidation zone 14 corresponds approximately to such ratio in the gaseous withdrawal stream 28, inasmuch as there is negligible oxygen consumption throughout the various steps of selective condensation preceding withdrawal stream 28.

Attention is now directed to the oxidation zone 14 from which flows liquid as a slip stream 21 to debutanizing zone 29. Said debutanizing zone is adapted to permit the selective condensation of a debutanized TBA stream 33 and the selective condensation of said previously identified IB stream 27, which helps to form recycle IB stream 12. The liquid slip stream 21 contains some dissolved nitrogen, oxygen, carbon monoxide and carbon dioxide, and a stream of such gas is vented through line 31 to gas withdrawal line 28, where they merge to form gas withdrawal line 32.

After liquid slip stream 21 has been debutanized in debutanizing zone 29, it flows as stream 33 to a decomposition zone 34. By treating the debutanized liquid at 260°-320° F. for 2-8 hours, most of the TBHP is decomposed to provide TBA and $O_2$. The thus generated $O_2$ can be withdrawn through controlled outlet 35.

After most of the TBHP has thus been decomposed, the liquid effluent stream 36 is directed from the decomposition zone 34 to distillation zone 37. An overhead stream 38 consists of acetone, methanol, and TBA. A bottoms stream 39 consists of a mixture of those high boiling components (HBC) boiling above TBA plus a sufficient amount of TBA to assure a molar ratio of TBA to TBHP greater than one. The bottoms stream 39 can be sent through a divider to allocate a portion to catalyst recycle stream 19 and a portion to fuel withdrawal line 40.

Attention is called to a control system 41 adapted to maintain the concentration of HBC (high boiling components) within the liquid in oxidation zone below 8% of the oxidate. Oxidation zone 14 is maintained at reasonably stable conditions, so that analyses of daily samples or hourly samples are usually adequate for fine tuning of the system. The drawing shows such control system generically to embrace either periodic sampling or continuous monitoring with feedback regulation of flow rates to maintain the HBC concentration in the oxidate less than 8%. The drawing has symbolic showing of communication lines 42, 43, 44 from lines 39, 21, and 38, respectively, to control system 41. Control system 41 preferably maintains the concentration of HBC in the oxidate below 8%. When there are sufficiently favorable conditions throughout the system, then a fraction of such HBC stream 39 can be diverted from fuel withdrawal line 40 and directed by catalyst recycle line 19 to oxidation zone 14. Under appropriate conditions, there is zero flow in line 19, symbolized by the dotted line.

Overhead stream 38 flows to a cleanup zone 45 in which such stream is subjected to 375°–475° F. for 1–10 minutes, thereby decomposing TBHP residues. The liquid effluent stream 46 represents the principal product of the present invention, and is a TBA stream suitable for use in motor fuels. Such stream also contains $Me_2O$ and MeOH.

The description of the drawing exemplifies some preferred embodiments of the invention, but is not intended to be limiting of the invention, which is defined in the appended claims. Various modifications of the invention are possible without departing from the scope of the appended claims.

We claim:

1. The method of preparing a motor fuel blending component which consists of:

maintaining in an oxidation zone a liquid consisting of dissolved isobutane and oxidate, said oxidate comprising dissolved byproducts, tertiary butyl hydroperoxide, and tertiary butyl alcohol, solubilized molybdenum catalyst in a concentration corresponding to from about 1 to about 1,000 parts per million of isobutane, while injecting into the liquid a gas comprising oxygen and while injecting into the liquid a mixture of recycled and fresh isobutane;

maintaining the liquid in said oxidation zone at a temperature within the range from 240° F. to 310° F. at a pressure adapted to maintain much of the isobutane in the liquid phase, said pressure being within the range from 200 to 1000 psig;

controlling product withdrawal rate and isobutane injection rate to provide a residence time within the range from about 3 to about 10 hours;

transferring from said oxidation zone a liquid stream, and directing said liquid stream through a debutanizing zone, to provide a debutanized liquid stream, and to provide a stream of isobutane recycled from the liquid, and to provide a withdrawn vapor stream comprising nitrogen, oxygen, carbon monoxide, and carbon dioxide;

transferring from said oxidation zone a vapor stream comprising nitrogen, oxygen, carbon monoxide, carbon dioxide, and isobutane, said vapor stream being subjected to partial condensation to provide a stream of isobutane recycled from a vapor zone of the oxidation zone, and to provide a withdrawn vapor stream comprising nitrogen, oxygen, carbon monoxide and carbon dioxide;

directing said debutanized liquid stream to a thermal decomposition zone maintained at a temperature within the range from about 260° F. to about 320° F. for from about 2 to about 8 hours to decompose a significant portion of the tertiary butyl hydroperoxide to form tertiary butyl alcohol and oxygen, and withdrawing a stream of oxygen from said decomposition zone;

transferring liquid from said decomposition zone for transfer to a distillation zone in which there is a distillate stream comprising acetone, methanol, and tertiary butyl alcohol which is taken overhead, and in which there is a residual liquid stream containing measurable amounts of tertiary butyl hydroperoxide, sufficient tertiary butyl alcohol to provide a unit weight ratio of tertiary butyl alcohol to tertiary butyl hydroperoxide greater than one, byproducts which are not completely codistilled with tertiary butyl alcohol, and molybdenum catalyst;

withdrawing said residual liquid stream;

subjecting said distillate stream to treatment in a peroxide clean-up zone, said treatment consisting of heating the liquid at from 375° F. to 475° F. for a time of from 1 minute to 10 minutes to provide a motor fuel blending component; and withdrawing from the peroxide clean-up zone a motor fuel blending component product stream containing tertiary butyl alcohol as the major product of the process, said stream also containing methanol.

2. The method of claim 1 in which the oxidation zone has a temperature from about 260° F. to about 300° F., a pressure from about 200 to 1000 psig and a residence time of from about 4 to about 6 hours.

* * * * *